US008828696B2

(12) United States Patent
Dailey et al.

(10) Patent No.: US 8,828,696 B2
(45) Date of Patent: Sep. 9, 2014

(54) USE OF PENICILLIN G PROCAINE AS A SELECTIVE ANTIMICROBIAL AGENT IN THE PRODUCTION OF ALCOHOL BY FERMENTATION

(75) Inventors: Kevin E. Dailey, Suwanee, GA (US); Sanjoy Ganguly, Hamilton, OH (US); Kevin L. Kauers, Norcross, GA (US); Limei Tang, Duluty, GA (US); Daniel W. Thon, Atlanta, GA (US)

(73) Assignee: Lallemand Specialites, Inc, Milwaukee, WI (US)

( * ) Notice: Subject to any disclaimer, the term of this patent is extended or adjusted under 35 U.S.C. 154(b) by 815 days.

(21) Appl. No.: 12/314,240

(22) Filed: Dec. 5, 2008

(65) Prior Publication Data

US 2010/0143307 A1    Jun. 10, 2010

(51) Int. Cl.
*C12P 7/06*    (2006.01)
*C12G 3/02*    (2006.01)
*A01N 43/90*   (2006.01)

(52) U.S. Cl.
CPC ... *C12P 7/06* (2013.01); *C12G 3/02* (2013.01); *A01N 43/90* (2013.01); *Y02E 50/17* (2013.01)
USPC .............................. 435/161; 426/11; 435/244

(58) Field of Classification Search
None
See application file for complete search history.

(56) References Cited

U.S. PATENT DOCUMENTS

| | | | |
|---|---|---|---|
| 2,964,406 | A | 12/1960 | Strandskov et al. |
| 3,120,514 | A | 2/1964 | Doyle et al. |
| 4,316,956 | A | 2/1982 | Lutzen |
| 4,568,644 | A | 2/1986 | Wang et al. |
| 5,100,791 | A | 3/1992 | Spindler et al. |
| 6,184,001 | B1 | 2/2001 | Starnes |
| 2008/0138871 | A1 | 6/2008 | Smith et al. |

OTHER PUBLICATIONS

Day et al., J. Agric. Food Chem., 1954, 2 (5), pp. 252-258.*
Bayrock et al., Appl Microbiol Biotechnol (2003) 62:498-502.*
Loussouarn, S. (1982). Sensitivity of lactic cultures to certain antibiotics. Technique Laitiere 965, 49-50.*
Jowsey et al., Canadian Journal of Animal Science, 1959, 39:(1) 21-25.*
Aquarone, E., Penicillin and Tetracycline as Contamination Control Agents in Alcoholic Fermentation of Sugar Cane Molasses1. Appl Microbiol. Sep. 1960; 8(5): 263-268.
Bryskier, A., Anti Microbial Agents. 2005, Ch. 5, 113-162.
Clark et al., eds., The Chemistry of Penicillin. 1949, pp. 660; 667-669, call No. RS 165 P38 C4.
Echegaray et al., Fed-batch culture of *Sacchoromyces cerevisiae* in sugar-cane blackstrap molasses: invertase activity of intact cells in ethanol fermentation. Biomass and Bioenergy. Jul. 2000:19(1):39-50.
Holm, K.A., Automated colorimetric determination of penicillin in fermentation samples using a molybdoarsenic acid-mercuric chloride reagent. Anal Chem. Apr. 1, 1972;44(4):795-9. doi: 10.1021/ac60312a040.
Jacques et al., eds., The Alcohol Textbook. 4th Edition. Nottingham University Press, Nottingham, UK, 2003, 448 pages.
Narendranath et al., Urea hydrogen peroxide reduces the numbers of lactobacilli, nourishes yeast, and leaves no residues in the ethanol fermentation. Appl Environ Microbiol. Oct. 2000;66(10):4187-92.
Plumb, D.C., Plumb's Veterinary Drug Handbook.5th Edition. Blackwell Publishing, 2005, pp. 601-611.
Rusling et al., Immobilized enzyme-based flowing-stream analyzer for measurement of penicillin in fermentation broths. Anal Chem. Jul. 1976;48(8):1211-5.

* cited by examiner

*Primary Examiner* — Irene Marx
(74) *Attorney, Agent, or Firm* — Nutter McClennen & Fish LLP

(57) ABSTRACT

A process for the use of low concentration levels of Penicillin G Procaine to eliminate or control the growth of unwanted or undesirable bacteria (contaminating bacteria) in the fermentation production of alcohol without inhibition of the growth or replication of the yeast.

1 Claim, No Drawings

USE OF PENICILLIN G PROCAINE AS A SELECTIVE ANTIMICROBIAL AGENT IN THE PRODUCTION OF ALCOHOL BY FERMENTATION

FIELD OF THE INVENTION

The present invention relates to the use of a selective Beta-lactam antimicrobial in the production of fuel alcohols, beverage alcohols and industrial alcohols by fermentation to control the growth of non-preferred, contaminating microorganisms during the yeast propagation and fermentation phase of production, wherein the selected antimicrobial is Penicillin G Procaine.

BACKGROUND OF THE INVENTION

Today, the production of bio-fuels, as an alternate or a substitute to gasoline is deemed as a potential strategy to contend with the rising demands of oil for energy. United States alone consumes about 25% of the total world's production of oil while it has less than 3% of the world's oil reserve. The recent expansion of the bio-fuels industry has fueled the popularity and increased awareness of the effects of ethanol on the environment, economy and US national policy. Antimicrobials have been used in fermentation during the production of fuel alcohol since its inception dating back to the 1970's. The co-products (distillers grains) resulting from these fermentations have been fed to livestock increasingly over the past 3 decades with a particularly sharp increase of 340% from 1999 to 2005 to 8.35 million metric tons of distillers grains in the United States alone. Most (98%) of the distillers grains in North America come from plants that produce ethanol for oxygenated fuels.

Alcohol is produced by yeast fermentation, of carbohydrates primarily derived from starch-based or sugar-based feedstocks. This fermentation is provided by yeast, specifically the microorganism *Saccharomyces cerevisiae* that ferments the available carbohydrates to produce ethanol. The entire process of alcohol production is well documented in "The Alcohol Text Book", 4$^{th}$ edition, Jacques, Lyons & Kelsall, published by Nottingham University Press, 2003, which is incorporated herein by reference.

One of the important concerns with a conventional fermentation system is the difficulty of maintaining a clean, disinfected and sterile condition which is free from contaminating bacteria in the large-sized batches during the long fermentation period. Unfortunately, the optimum environment for fermentation is also extremely conducive to bacterial growth. If a batch becomes contaminated, not only must the fermentation mixture (i.e. the yeast, feedstock, nutrients, water, etc.) be discarded, but the entire fermentation vessel must be emptied, cleaned, disinfected or sterilized as per the protocol of a production facility. This process adds unwanted costs and loss of production.

It is common in current commercial fermentation processes for contaminating bacteria to infect the fermentations and consume the available carbohydrate consequently causing less carbohydrate availability to the preferred yeast fermentation. Contamination by bacteria is very costly to the ethanol producer and a variety of control methods are utilized to limit this event. It is commonplace in most ethanol producing facilities to utilize caustic washing via clean in place systems.

The origin of these contaminants is multi-faceted and is being studied and contemplated by both researchers and producers. It is generally accepted that much of the bacteria originates from the incoming feedstock since the starch crops are often contaminated with bacteria from the field and storage silos. Jet cooking the fermentation substrate (mash) helps lower the bacteria count, but does not completely eliminate the contaminants as this process is not a sterilization procedure. Bacterial contamination is unavoidable because these production facilities are not sterile environments like those commonly found in the pharmaceutical industry.

With the increased popularity of the bio-fuels industry, alcohol productions along with distillers co-products have increased steadily over the years. This has caused heightened awareness and concerns regarding the use of antimicrobials during the fermentation process and the possibility that antimicrobials "carry through" to the resulting distillers co-products.

The industry is currently awaiting more direct guidance from the Food & Drug Administration (FDA) and the Center for Veterinary Medicine (CVM) as well as certain state agencies (where applicable) on the allowable use of antimicrobials as a processing aid in ethanol production.

An economical method to selectively control contaminating bacteria is needed. The method must utilize smaller amounts of an antibiotic or a combination of antibiotics than currently being used to target and act as bactericidal and/or bacteristatic to control contaminating bacteria in fermentation, such as a bacterial contaminant found in the production of fuel alcohols, beverage alcohols and industrial alcohols while improving production yield. Additionally, distillers co-products from the fermentation must be safe for direct feeding to animals, i.e., the antibiotic used must not be detectable in the distillers co-products in order to comply with increasing state and federal regulation. From the alcohol producer's point of view, the antibiotic needs to be cost effective and would be of more value if it did not have a deleterious effect on the yeast, thus producing more alcohol. Further, the antibiotic needs to be less susceptible to resistance by the targeted bacteria and be effective in low concentrations while not carrying through to the distillers grams.

SUMMARY OF THE INVENTION

The methods provided herein employ Penicillin G Procaine compositions to reduce or inhibit the growth of undesired bacteria during alcohol fermentation. The compositions are used in industrial fermentation systems to reduce the growth of competing bacteria and enhance efficiency and/or yield during the industrial fermentation of fuel, beverage and industrial alcohols.

It is, therefore, an object of the present invention to provide a method for increasing the amount of alcohol produced during large scale alcohol production and minimizing residual antibiotic in the distillers co-products. The method is achieved by introducing an antibiotic, Penicillin G Procaine, into a vessel used during alcohol production to render an ideal environment for a fermentation mixture created thereby. The Penicillin G Procaine functions to substantially reduce any deleterious effects of at least one contaminant bacteria present in the fermentation mixture while not having any deleterious effects on the yeast. The Penicillin G Procaine is added to the vessel in an amount ranging from at least 0.1 ppm to about 5 ppm of the fermentation mixture. Penicillin G Procaine is from the Beta-lactam family of antibiotics, and more specifically is a Penicillin derivative, benzyl penicillin in a unique combination with a substituted amino ester group more specifically 2-(diethylamino) ethyl 4-aminobenzoate commonly called Procaine.

It is also an object of the present invention to provide a method wherein the antibiotic is added in an amount ranging from 0.25 to 3 ppm of the fermentation mixture.

It is another object of the present invention to provide a method wherein the alcohol produced is ethanol.

It is a further object of the present invention to provide a method wherein the vessel is a fermentation tank and the antibiotic is introduced therein.

It is still another object of the present invention to provide a method wherein the vessel is a yeast propagation tank and the antibiotic is introduced therein.

It is yet another object of the present invention to provide a method wherein the fermentation mixture is derived from any feedstock selected from the group consisting of, but not limited to: corn, wheat, triticale, barley, cassava, rye, graded starch stream rendered from the feedstocks, sugar cane, sugar beet, molasses, rice straw, potato waste, wood waste, switch grass, pine and other wood derivatives, municipal waste, food waste, alcoholic and non-alcoholic beverage industry waste and mixtures thereof.

It is also an object of the present invention to provide a method wherein in addition to alcohol being produced co-products result and the antibiotic in these co-products is low or at a non-detectable level.

It is still a further object of the present invention to provide a method wherein the antibiotic functions to bind and block peptidases that cross-link the glycan molecules and interrupt the completion of the cell wall of the contaminating bacteria. More specifically, the antibiotic binds to enzymes, such as DD-transpeptidase that link the peptidoglycan molecules in the bacteria thereby making the cell wall of contaminating bacteria weak at growth sites and become osmotically fragile.

It is a further object of the present invention to provide a method by which the antibiotic functions to cause osmotic fragility, generating a bactericidal effect, making the weakened cell subject to lysis, thus controlling the deleterious effects of at least one contaminating bacteria but not limited to *Lactobacillus brevis, Lactobacillus fermentum, Lactobacillus paracasei, Lactobacillus pentosus/plantarum, Lactobacillus reuteri, Lactobacillus buchneri, Lactobacillus plantarum/pentosus* and other *Lactobacillus* spp., present in said fermentation mixture while being unable to harm the yeast cell wall rendering the antibiotic harmless to yeast during fermentation.

It is a yet another object of the present invention to provide a method by which the antibiotic functions as a bactericidal and or bacteristatic agent only, without harming the yeast regeneration through metabolism and budding during fermentation.

It is still a further object of the present invention to provide a fermentation mixture used in the production of ethanol comprising of yeast, carbohydrates and Penicillin G Procaine, wherein the Penicillin G Procaine slowly inhibits growth of microorganisms competing for the sugars thereby increasing the amount of alcohol produced from the fermentation mixture and offering unique bacteria control into late stages of fermentation.

It is another object wherein the Penicillin G Procaine is present in the fermentation mixture in an amount ranging from 0.1 ppm to about 5 ppm of the fermentation mixture.

It is another object wherein the Penicillin G Procaine fosters the growth and replication of *Saccharomyces cervisea* yeast in the fermentation mixture.

It is still another object wherein the Penicillin G Procaine at concentrations of 0.1 ppm of the fermentation mixture fosters additional yeast cell replicate.

It is still another object wherein the Penicillin G Procaine at concentrations of 30 ppm of the fermentation mixture fosters additional yeast cell replicate.

It is another object wherein the Penicillin G Procaine is able to control the industry isolated *Lactobacillus brevis*, bacterial growth at a low minimum inhibitory concentration of 1.0 ppm of the fermentation mixture.

It is another object wherein the Penicillin G Procaine is able to control the industry isolated *Lactobacillus fermentum*, bacterial growth at a low minimum inhibitory concentration of 0.1 ppm of the fermentation mixture.

It is also an object of the present invention to provide a method for controlling the growth of lactic acid bacteria in a fermentation process for the production of alcohol. The method includes the steps of adding a minimum inhibitory concentration of Penicillin G Procaine and the Penicillin G Procaine becoming part of a fermentation mixture used in making alcohol, wherein the vessel is susceptible to lactic acid bacteria, and wherein the addition of the minimum inhibitory concentration of Penicillin G Procaine to the vessel controls the growth of lactic acid bacteria.

It is yet another object of the present invention to provide a method for controlling the growth and multiplication of lactic acid bacteria over a prolonged long period of time (48 hours) in a fermentation process for the production of alcohol.

It is also an object of the present invention to provide a method for controlling the growth and multiplication of lactic acid bacteria with a prolonged low concentration of Penicillin G in a fermentation process for the production of alcohol. The method includes the steps of adding a minimum inhibitory concentration of Penicillin G Procaine and the Penicillin G Procaine becoming part of a fermentation mixture used in making alcohol, wherein the vessel is susceptible to lactic acid bacteria, and wherein the addition of the minimum inhibitory concentration of Penicillin G Procaine to the vessel controls the growth and multiplication of lactic acid bacteria over a prolonged period of time.

These and other objects, features and advantages of the present invention will become apparent after a review of the following detailed description of the disclosed embodiments and claims.

DETAILED DESCRIPTION OF THE INVENTION

As previously stated, with the increase in demand, the production of commercial alcohol, specifically fuel grade alcohol, predominantly ethanol, past and current legislation has led to a trend of investment into manufacturing capacity and development of production efficiencies.

Over the past six decades Penicillin has gained popularity as a commonly used antimicrobial for use in animal and human clinical health as referenced in numerous patents. The chemistry of Penicillin was well documented in 1949 by Clarke et al. The Chemistry of Penicillin, pages 660, 667-669, Call No. RS 165 P38 C4. More than three decades ago U.S. Pat. No. 4,316,956 stated the use of antibiotics in fermentation processes. Patent application such as U.S. Patent Application Publication No 20080138871 lists Penicillin and Tetracycline as examples of antibiotics that can be used during fermentation. U.S. Pat. No. 5,100,791 referenced Penicillin and Streptomycin as antibacterial agents for use in lab scale cellobiose fermentation. Aquarone in Applied Microbiology, 1960, 8:263-268 mentions the use of Penicillin and Tetracycline as contamination control agents in alcoholic fermentation of sugarcane molasses. Another U.S. Pat. No. 4,568,644 describes a fermentation method to produce ethanol where the said antibiotic is Penicillin.

In the past Penicillin of the type G and V or their potassium salts were used in fermentation and their effects and determination in fermentations were vastly studied as depicted in Analytical Chemistry, Vol. 44, No. 4, April 1972, page 795; Analytical Chemistry, Vol. 48, No. 8, July 1976, page 1211; Biomass and Bioenergy, Vol. 19, Issue 1, July 2000, Pages 39-50. Ingledew mentions the use of Penicillin G in his article in Applied and Environmental Microbiology, October 2000, p. 4187-4192, Vol. 66, No. 10; U.S. Pat. No. 6,184,001.

All previously disclosed fermentation processes describe the use of Penicillin or Penicillin G or V as processing aid in yielding alcohol. Unlike any previously disclosed applications of the use of Penicillin, the present invention illustrates that Penicillin G Procaine is efficacious for use in the commercial production of alcohol. Furthermore, the present invention relates to a method of use for Penicillin G Procaine having a significantly different set of criteria for efficaciousness than that involved with human clinical health.

As employed in accordance with a preferred embodiment of the present invention, Penicillin G Procaine is effective against bacteria commonly found in the production of fuel alcohols, beverage alcohols and industrial alcohols, and is more effective than other commonly used antibiotics against industry-specific isolated bacteria. The alcohols produced for fuel, beverage and industrial use are oftentimes manufactured in the same facility utilizing the same fermentation technique. The use and effectiveness of Penicillin G Procaine are realized to the same degree in the same fermentation process producing ethanol as for all three categories: fuel, beverage and industrial applications.

Briefly, the present invention provides a method for increasing the amount of alcohol produced during large scale alcohol production. The method is achieved by introducing an antibiotic as an active agent to a vessel used during alcohol production to render an ideal environment for a fermentation mixture when combined with the antibiotic for fermenting the fermentation mixture into the desired alcohol. The Penicillin G Procaine functions to substantially reduce any deleterious effects of at least one contaminant bacteria present in the fermentation mixture while not having any deleterious effects on the yeast. The active agent, Penicillin G Procaine is added to the vessel in an amount ranging from at least 0.1 ppm to about 5 ppm of the fermentation mixture.

In addition, Penicillin G Procaine, when used in accordance with the present invention, has the propensity to render a low (or no) detection level in distillers co-products compared to other antimicrobial agents when added during the alcohol production process in amounts/concentrations disclosed in the present application. Penicillin G Procaine used in accordance with the present invention is not deleterious to the preferred fermentation organism, yeast (*Saccharomyces cervisea*), in the low oxygen environment associated with the production of alcohol. In addition, Penicillin G Procaine has a very specific mode of action when used during fermentation. Although a Beta-lactam, its mode of action is very specific and makes it unlike any other antimicrobial commonly used in the production of alcohol.

Penicillin G is known for its activity on gram positive bacteria as sited in numerous literature and industrial handbooks as in pg 601-611, Plumb's Veterinary Drug handbook by Donald C. Plumb, Blackwell Publishing, 5th edition, 2005 and pg 113-162, Chapter-5, Anti Microbial Agents, Andre Bryskier, 2005. In accordance with the present invention Penicillin G Procaine showed advantageous antibacterial activity for gram positive forms of bacteria especially those isolated from fuel ethanol producing plants compared to industrial antibiotics currently in use. The advantageous activity of Penicillin G Procaine, as shown in this application with typical bacterial examples, was found in particular on *Lactobacillus* species. The *Lactobacillus* species of lactic acid producing bacteria may be but not limited to *Lactobacillus brevis, Lactobacillus fermentum, Lactobacillus paracasei, Lactobacillus pentosus/plantarum, Lactobacillus reuteri, Lactobacillus buchneri, Lactobacillus plantarum/pentosus* and other *Lactobacillus* spp.

Penicillin G Procaine Operation

The Penicillin G Procaine added during the alcohol production process in accordance with the present invention is a very effective antibiotic against lactic acid bacteria such as *Lactobacillus* species. The prevention of the growth of lactic acid bacteria during alcohol production is beneficial. The prevention of bacterial growth over a prolonged period and at a low concentration of antibiotic makes the Penicillin G Procaine a novel antimicrobial for its use in fermentation processes.

The Penicillin G Procaine and all Penicillin derivatives produce a bactericidal effect by inhibiting bacterial cell wall synthesis. The cross-linking of peptides on the monosaccharide chains is prevented by Penicillin G Procaine and is predicted to be due to the similarity in the structure of a Penicillin segment and the cell wall peptide chain. Penicillin binds to enzymes, specifically the DD-transpeptidase that link the peptidoglycan molecules in the bacteria thereby making the cell wall weak at growth sites and osmotically fragile which renders the cells to lysis, thus controlling the contaminating bacteria growth and replication.

Gram-positive bacteria possess a thick cell wall composed of a structural sugar polymer bound in a covalent fashion to short peptide units. These polysaccharide portions of the peptidoglycans are made of repeating units of N-acetylglucosamine linked to N-acetylmuramic acid (NAG-NAM). The peptide chain varies, but starts at L-Ala and ends with D-Ala with diaminopimelate (DAP) in the middle. DAP provides a linkage to the D-Ala residue on an adjacent peptide. The cell wall synthesis for the bacteria is completed when a cross link between the two peptide chains attached to polysaccharide backbones takes place. The cross linking is catalyzed by the enzyme transpeptidase. First, the terminal alanine from each peptide is hydrolyzed; secondly one alanine is joined to lysine through an amide bond. Penicillin type of Beta-Lactams binds at the active site of the transpeptidase enzyme that cross-links the peptidoglycans. It does this by mimicking the D-alanyl-D-alanine residues that would normally bind to this site. The antibiotic irreversibly inhibits the enzyme transpeptidase by reacting with a serine residue in the transpeptidase. This reaction is irreversible and so the growth of the bacterial cell wall is inhibited. Due to this inhibition of the cell wall structure, the deformities render the cell wall of the contaminating bacteria susceptible to osmotic imbalance thus making them osmotically fragile which ultimately causes the cell to lysis.

Even though all classes of penicillin and its derivatives have generally a similar method in their actions towards lactic acid bacteria, at least parts of antibacterial effects under different environmental conditions can have certain pronounced or a more specific activity towards a species of bacteria which may not be manifested to the same degree by the same antibiotic type on a similar lactic acid bacterial species under different environmental or chemical conditions. The Penicillin G Procaine shows some unique characteristics in its actions towards the lactic acid bacteria found in the ethanol production facilities. The Penicillin G Procaine displays a tendency to stay in the fermentation mixture longer than the conventional Penicillin salts like Penicillin G Potassium or Penicillin V type of Beta-lactams. The reason for the longer duration and the ability to use lower concentration of antibiotic during fermentation can be attributed to the ammonium salt of the Procaine which binds to the carboxylic moiety of the penicillin group. During a fermentation cycle the Penicillin G Procaine is hydrolyzed to penicillin G and acts as a repository form of Penicillin G. This specific method of inhibiting cell wall formation in susceptible bacteria over a longer period with the use a of lower concentrations of antibiotic by interfering with the cross-linking and destabilizing the cell wall surface, as applied in accordance with the present invention has been determined to be unique to Penicillin G Procaine and not like any other Beta-lactam commonly used in alcohol production.

The primary bacteria of concern in alcohol production processes are gram positive bacteria of, but not limited to, the *Lactobacillus* and *Pediococcus* species. Penicillin G Procaine utilized in alcohol production in accordance with the present invention efficaciously controls gram positive bacteria specifically present in the production of fuel alcohol, beverage alcohol and industrial alcohol.

Penicillin G Procaine works by inhibiting cell wall formation at the cellular level. The cell wall differences between the gram-positive and gram negative bacteria make the Penicillin G Procaine more effective on the gram-positive bacteria. The gram-positive bacteria has a thick cell wall comprising of peptidoglycan followed by the cell membrane whereas the gram-negative bacteria have another outer membrane below which lies the thin peptidoglycan layer followed by a thin inner cell wall. Penicillin G Procaine cannot penetrate the outer membrane of gram-negative bacteria easily; hence, penicillin as a bactericidal agent is more effective on most gram-positive bacteria. The outer membrane of the gram-negative bacteria has special membrane channels formed by porin proteins that span the outer membrane. The size of the porin can be altered by the bacteria as a defense mechanism to resist harmful chemical such as Penicillin or its derivatives. The yeast cell wall is thick and rigid in structure with an outer layer of Chitin, followed by glycoprotein and mixed glycans. It is believed that this varied composition of the yeast cell wall works as a protecting layer against Penicillin type Beta-lactam antibiotics. U.S. Pat. No. 2,964,406 reports that in fermentation reactions in making alcohol, the activity of yeast was found to increase in presence of Penicillin.

Upon the consumption of sugar during fermentation, gram positive bacteria produce organic acids. These contaminating bacteria are able to convert one mole of glucose into two moles of lactic acid. Therefore, for every gram of lactic acid formed, nearly two grams of glucose is lost which represents a one-gram loss in alcohol produced by the preferred organism (that is, yeast). This occurrence is very costly to the producer where a 1% lactic acid production level represents an approximate loss of 1% of alcohol by weight. The detrimental effect of lactic acid is a well documented fact as it occurs in many fermentation processes. The economics and efficiency of fermentation processes are such that ethanol producers cannot tolerate any such loss of production. If antibiotics are not used, a 1 to 5 percent loss in ethanol yield is common. A fifty million-gallon (annual capacity) fuel ethanol plant operating with a lactic acid level of 0.3 percent weight/weight in its distillers beer is losing roughly 570,000 gallons of ethanol every year due to bacterial contamination.

Penicillin G Procaine, when used in accordance with the present invention in the production of alcohol, exhibits a high degree of effectiveness when controlling the growth and/or lysing of contaminant bacteria. The present invention offers several advantages to using Penicillin G Procaine over the use of other antibiotics in the commercial alcohol production process. Low concentration levels of Penicillin G Procaine, in accordance with the present invention, were found to control the growth of bacteria over a longer period of fermentation time. In fact, lower concentration levels of Penicillin G Procaine are needed to achieve the same amount of bacterial control compared with other antibiotics including other penicillin salts known in the art. Penicillin G Procaine also seems to have a slower discharge rate under ambient fermentation conditions thereby spreading the antibiotic effectiveness over a longer period in the fermentation vessel. It is probable that under certain fermentation conditions the Penicillin G Procaine stays in equilibrium with the free and bound Penicillin. In favorable conditions, the degradation of the free Penicillin is minimized thereby providing a long period of coverage against the bacteria present in the fermentation vessel. Therefore, Penicillin G Procaine is capable of eliminating certain contaminating bacteria more systematically and effectively than other penicillin salts and other commonly used antibiotics with a lower dose amount per fermentor. Also, and due to the small concentration levels of Penicillin G Procaine used in accordance with the present invention, the antibiotic does not carry through to the co-products produced. That is, there is no detectable antimicrobial in the distillers co-products tendered from fermentations employing Penicillin G Procaine used in accordance with the present invention.

Since antibiotics are costly, lower levels used during the alcohol production process relates directly to a reduction in the cost per liter of alcohol when produced in accordance with the present method.

The present invention provides methods and compositions for enriching the fermentation mixture to optimize and foster the growth and replication of *Saccharomyces cervisea* yeast while reducing or preventing growth or replication of undesirable bacteria.

Penicillin G Procaine Compositions

Penicillins are produced by many fungi particularly of the *Penicillium* and *Aspergillus* species. Penicillin G Procaine is from the peptide group of antibiotics whose synthesis is described in U.S. Pat. No. 3,120,514 as incorporated herein by reference. It is specified in the FDA's Code of Federal Regulation, Title 21 as an animal drug for use in animal feed ref. CFR558.460. Penicillin G Procaine also known as APPG, Aqueous Procaine Penicillin G, Benzylpenicillin Procaine, Procaine Penicillin G, Procaine Benzylpenicillin is the Procaine monohydrate salt of Penicillin G. One mg of Penicillin G Procaine is equivalent to 900-1050 USP Units.

Penicillin G Procaine-based antibiotics, of the Bactenix® line of products available from North American Bioproducts Corporation (NABC) in particular Bactenix® V50, Bactenix® V60, V60SP or V60SPK are referred to in the present invention as Penicillin G Procaine. Bactenix® V60 or V60SP or V60SPK has a composition that is stabilized in a dry form and is preferably added in the alcohol production process to a vessel during the propagation and fermentation steps to combine with the fermentation mixture prior to, during or after the introduction of *Saccharomyces* yeast to the process. However, it is contemplated that the Penicillin G Procaine can be added to any of the vessels or tanks used during the production of alcohol, such as the mix tank, liquification tank, saccharification tank, propagation tank and/or fermentor.

Penicillin G Procaine as the specific antimicrobial agent functions to reduce, eliminate or control the growth of unwanted or undesirable bacteria in a fermentation mixture without inhibiting the growth or replication of a microorganism of interest (yeast). The methods described herein utilize the composition to enrich the fermentation mixture to foster optimal growth of the desirable microorganism during the propagation and fermentation phase of commercial alcohol production and limit the undesirable end products. Penicillin G Procaine may be used as a single ingredient finished product antibiotic, as a component of a combinatory finished product, or in conjunction with any other antimicrobial known as useful in this process by those skilled in the art.

Method of Increased Alcohol Production

Large scale alcohol fermentation is often done in a two-step process. First one propagates the yeast in a propagation tank forming an inoculum. Then this inoculum is transferred to a much larger fermentation tank (fermentor) and mixed with a previously created fermentation mixture/mash. Generally, the fermentation mixture is created by adding water and fermentation substrates/feedstock together in a mixing tank, transferring this mixture to a liquification tank where alpha-amylase is added and then transferring this mixture to a saccharification tank where additional enzymes are added. Many plants may also add alpha-amylase to the mix or slurry tank and reapply if needed in the liq tanks. Many others may use simultaneous saccharification and fermentation where the gluco-amylase is added to the fermentor where sugar breakdown and fermentation takes place simultaneously. The resulting fermentation mixture generally contains feedstock (carbohydrates), nutrients, water, etc. and is often referred to as mash. The mash used for fermentation usually containing between 30-36% solids. The nutrients help the yeast cells grow to be strong and healthy enabling the yeast to perform better in the fermentor, giving a much desired fermentation that completes the process by exhausting the available starch.

The present invention, as briefly discussed above provides a method for increasing the amount of alcohol produced during large scale alcohol production. The method involves introducing this antibiotic as an active agent, preferably, to a fermentation mixture in a vessel during alcohol production to render an ideal environment for fermentation of the fermentable mixture into the desired alcohol by yeast that is capable of fermenting the fermentation mixture into the desired alcohol under conditions suitable to promote fermentation. Although in accordance with a preferred embodiment, the antibiotic is added to the fermentation tank or the propagation tank, the antibiotic may be added to any one of the tanks used during the alcohol production process as it will ultimately combine with the fermentation mixture. The active agent functions to substantially reduce any deleterious effects of at least one of the contaminating bacteria present in said fermentation mixture while not having any deleterious effects on the yeast.

Specifically, the active agent is added to the mixture in an amount ranging from at least 0.1 ppm to about 5 ppm of fermentation mixture.

In large scale industrial production of ethanol Penicillin G Procaine works best if the fermentation temperature is maintained between approximately 30-38° C. and the pH is maintained between approximately 2.5 to 8, more specifically approximately 4.5 to 6.5. In industrial alcohol fermentation, the fermentation mixture to which the Penicillin G Procaine composition is added is an extremely large volume (10,000-1,000,000 gallons). In accordance with the present invention, the Penicillin G Procaine is preferably added during the propagation and fermentation phase of the alcohol production in an effective amount for controlling or lysing of undesirable bacteria in amounts of at least 0.1 ppm, preferably at least 0.5 ppm of Penicillin G Procaine per amount of fermentation mixture to be treated, preferably between 0.5 to about 5 ppm, and most preferably 0.25 to 3 ppm.

Bacterial cells contemplated for treatment by the present methods include, but are not limited to, bacterial cells found to be contaminating systems of commercial significance, such as those used in the production of commercial fuel alcohols, beverage alcohols and industrial alcohols regardless of feedstock. Such bacteria include, but are not limited to, organisms such as *Lactobacillus* spp., *Pediococcus* spp. and *Brevibacterium* spp. found during ethanol production.

Benefits of using Penicillin G Procaine

The use of such small amounts of Penicillin G Procaine does not deleteriously affect the fermentation production of alcohols in any manner, does not produce any undesirable side effects to the yeast, does not carry through to the distillers co-products and results in an increase in the amount of alcohol produced.

The Penicillin G Procaine compositions and methods provided herein are suitable to reduce, inhibit, or eliminate undesirable or contaminating bacterial species and strains commonly found in the production of ethanol while increasing the amount of ethanol produced. Thus, while antimicrobial use during alcohol production is not a new concept, it has been determined herein that a small amount of Penicillin G Procaine is an extremely efficacious and systematic control agent for the specific bacteria that are commonly found in the alcohol production environment. Specifically, Penicillin G Procaine at these concentration levels and at a prolonged slower release rate does not affect the yeast or its performance in any way, which along with the inability to bind to the chitin layer of the yeast or any component of the cell wall of the yeast, prevents the antimicrobial from harming the yeast. Yeast cells also have no peptidoglycan layer outside the cell, hence do not have the pertinent available enzymes to bind to the Penicillin G Procaine moiety. They do have enzymes present but there may not be compatible binding sites and hence no deleterious effects are noticed from the Beta-lactams. Not harming the yeast during fermentation is important because it results in greater alcohol production while also preventing the contaminating bacteria from consuming more carbohydrates.

The presence of undesirable bacteria in the fermentation can have the effect of reducing production rates of the desired alcohols, as well as promoting the production of undesirable by-products such as organic acids and glycerol. The use of Penicillin G Procaine results in enhanced production of the desired alcohol product produced by the yeast. The methods provided herein ate particularly useful because the feedstock or starting material in the alcohol production process is not sterile and therefore typically contain contaminating microorganisms.

Examples of feedstocks include (but are not limited to) corn, wheat, triticale, barley, cassava, rye, graded starch stream rendered from the aforementioned feedstocks, sugar cane, sugar beet, molasses, rice straw, potato waste, wood waste, switch grass, pine and other wood derivatives, municipal waste, food waste and beverage (alcoholic and non-alcoholic) industry waste. With such materials serving as feedstock it is not surprising that most commercial fermentations take place in the presence of significant bacterial contamination. *Lactobacilli* are the major contaminants in ethanol production and their presence and resultant lactic acid production reduces ethanol yield and creates a variety of stress factors that adversely affect yeast growth.

In the chemical antimicrobial agent marketplace, it is difficult work to identify a new antimicrobial that will offer efficacious control of bacteria specific to the alcohol production process that is not cost prohibitive. In this sense, it is unusual that such a small amount of Penicillin G Procaine would be effective in controlling undesirable bacteria (specific to this process) in a propagation cycle of alcohol production for approximately 10 hours. Furthermore, it is unexpected that such a small concentration of Penicillin G Procaine would be effective in controlling undesirable bacteria (specific to this process) in a fermentor for alcohol production for approximately 50 hours. This bacterial contamination in the propagation cycle or the fermentation cycle may be directly or indirectly controlled by the Procaine Penicillin G largely due to the efficacy of the antibiotic in controlling and keeping down the bacterial contamination, its non interference with the yeast thereby triggering a healthy yeast multiplication of the yeast, and minimizing the acid stresses detrimental to the ethanol producing capacity of the yeast. Thus, the process of the present invention provides the benefits of both: little or no undesirable side effects and extended production time efficacy with higher alcohol levels.

The antibiotics currently most often used at fermentation alcohol production plants are Streptomycin, Ampicillin, Virginiamycin, Tylosin, Oxytetracycline or Penicillin in their common salts when available. The commonly used Penicillin is the Penicillin V or G type with the G type being used more commonly as its potassium salt. There is no known or reported use of the Procaine form of Penicillin G in the production of alcohol. Among the above mentioned antibiotics used in the fuel ethanol industry, Virginiamycin is the one most frequently used in the United States due to its availability and use in animal feed as a drug. Virginiamycin had been used in this industry as a bactericidal agent as it has been widely marketed for its dual role in the biofuel industry, namely ethanol in particular, and for its marketability as an antibiotic drug in the animal feed and care industry. The usefulness and efficacy of the Penicillin G Procaine having a superior antimicrobial effect in controlling the contaminant bacteria is substantiated in this application. The application compares its use, effectiveness and worthiness for its method of use in the fuel ethanol industry against known "industry normal" bacteria presenting its comparisons to "widely used" antibiotic in the industry and also to its own salts form, the potassium salt of Penicillin G. The efficacy of the Penicillin G Procaine to subdue the bacteria during the fermentation ethanol production and its subsequent decomposition leaving no detectable residue in the distillers grain is also substantiated in this application.

Comparative Efficacy Study

The following examples depict the efficacy of Penicillin G Procaine in alcohol production by fermentation in accordance with the present invention and are not intended to limit the present invention, but are provided to aid in the understanding of the usefulness of Penicillin G Procaine, such as a Bactenix® line of products more specifically Bactenix® V60 or V60SP or V60SPK, in selectively controlling bacteria even when added in miniscule amounts.

The most commonly found microorganism in fuel ethanol producing plants is the *Lactobacillus fermentum* bacterium and is considered as an "industry normal" bacterium. This example compares the use of a Bactenix® line of products, Penicillin G Procaine-antibiotic versus Virginiamycin-antibiotic to control "industry normal" *Lactobacillus fermentum* bacterium. This trial uses an alcohol water mixture to assure total dissolving of antibiotics. This assures that the correct concentrations of antibiotics are going into the test wells and thereby preventing under dosing during the trial. All bacteria tested were industry specific isolates that were obtained from actual corn mash samples from fermentation alcohol production plants. The trial was set up as follows:

1. Dissolve 0.1 g of each of the antibiotics in 1 ml water and then add 5 ml of ethanol, vortex and bring up to 10 ml with sterile water to from a suspension.
2. Dilute the previous suspension 1:10 with sterile water. This gives a one mg/ml concentration.
3. Filter the suspension by running through a 0.2 µm syringe filter.
4. Add four µl broth in a centrifuge then add antibiotics to MRS (DeMan, Rogosa and Sharpe) broth at the concentrations required for the test.
5. Take four µl of a fresh 24-hour culture of the target organisms and add to the corresponding empty wells in a pre-labeled 24 well tissue culture plate.
6. Pipette one ml of the appropriate antibiotic media to each well of the plate.
7. Incubate at 33° C. for 24 hours.
8. Read plates for bacterial growth and re-incubate the plates at 33° C.
9. After 48 hours read and report the final results.

As displayed in Table 1 below, Penicillin G Procaine was found to be effective from 0.1 ppm while Virginiamycin was not effective against the industry standard *Lactobacillus fermentum* even at 0.5 ppm. At higher dosage of above 1 ppm Virginiamycin showed comparable effectiveness as Penicillin G Procaine against this gram positive bacterium.

TABLE 1

Virginiamycin (Bactenix® V100) vs. Penicillin G Procaine (e.g. Bactenix® V60) comparative efficacy analysis

| Concentration | V100 | V60 | V100 | V60 | V100 | V60 | V100 | V60 | V100 | V60 |
|---|---|---|---|---|---|---|---|---|---|---|
|  | 0.1 ppm | | 0.3 ppm | | 0.5 ppm | | 1 ppm | | 5 ppm | |
| *L. fermentum* | 1 | − | 1 | − | 1 | − | − | − | − | − |
|  | 1 | − | 1 | − | 1 | − | + | − | − | − |
|  | 1 | − | 1 | − | 1 | − | − | − | − | − |

Note:
White squares are 24 hour readings, shaded squares are 48 hour readings, a negative (−) sign is indicative of no observed growth, a positive (+) sign is indicative of some observed growth and a one (1) sign is indicative of substantial observed growth.

An alcohol production plant trial was completed to confirm and replicate the positive results found in the laboratory that Penicillin G Procaine (V60 or V60SP or V60SPK) was more effective than Virginiamycin (V100) in controlling bacteria encountered in ethanol production.

This trial was conducted at a 50 million gallon per year (m/g/y) dry grind fuel alcohol production facility utilizing corn as a fermentation substrate. Batch yeast propagation and fermentation process were utilized. Antimicrobials were added to the fermentor during the fill cycle at approximately 30% fill.

No other changes were made to the process or chemical additions that would influence the fermentation kinetics monitored during 3 sets of fermentor batches listed below. The fermentation data was accumulated at the end (drop) of the fermentation process for each of the fermentors. Fermentation kinetics was measured for three batch cycles including:

Set 1—"Pre Penicillin G Procaine trial"-10 fermentor batches using a level of 0.5 ppm Virginiamycin. See results in Table 2.

Set 2—"Penicillin G Procaine trial"-10 fermentor batches using a level of 0.5 ppm of Penicillin G Procaine. See results in Table 3.

Set 3—"Post Penicillin G Procaine trial"-10 fermentor batches using a level of 0.5 ppm of Virginiamycin. See results in Table 4.

TABLE 2

Virginiamycin control drop data - "Pre Penicillin G trial"

| Test # | Ferm # | Lactic % | Acetic % | EtOH v/v % | Glucose % |
|---|---|---|---|---|---|
| 1 | 2 | 0.59 | 0.02 | 15.66 | 0.36 |
| 2 | 3 | 0.584 | 0.04 | 15.31 | 0.31 |
| 3 | 4 | 0.59 | 0.04 | 15.46 | 0.16 |
| 4 | 5 | 0.41 | 0.03 | 15.39 | 0.26 |
| 5 | 1 | 0.59 | 0.02 | 15.66 | 0.36 |
| 6 | 2 | 0.71 | 0.04 | 15.64 | 0.27 |
| 7 | 3 | 0.71 | 0.04 | 15.52 | 0.26 |
| 8 | 4 | 0.85 | 0.04 | 15.58 | 0.31 |
| 9 | 5 | 0.56 | 0.04 | 15.40 | 0.29 |
| 10 | 1 | 0.79 | 0.13 | 15.16 | 0.3 |
| 10 | Batch average | 0.64 | 0.04 | 15.48 | 0.29 |

TABLE 3

Penicillin G Procaine test drop data - "Penicillin G trial"

| Test # | Ferm # | Lactic % | Acetic % | EtOH v/v % | Glucose % |
|---|---|---|---|---|---|
| 1 | 3 | 0.26 | 0.03 | 15.91 | 0.28 |
| 2 | 4 | 0.26 | 0.03 | 15.93 | 0.29 |
| 3 | 5 | 0.24 | 0.04 | 16.07 | 0.28 |
| 4 | 1 | 0.25 | 0.04 | 15.81 | 0.27 |
| 5 | 2 | 0.28 | 0.03 | 15.75 | 0.28 |
| 6 | 3 | 0.19 | 0.03 | 15.96 | 0.30 |
| 7 | 4 | 0.21 | 0.02 | 15.92 | 0.27 |
| 8 | 5 | 0.26 | 0.03 | 15.95 | 0.27 |
| 9 | 1 | 0.25 | 0.05 | 15.86 | 0.27 |
| 10 | 2 | 0.23 | 0.03 | 16.16 | 0.27 |
| 10 | Batch average | 0.24 | 0.03 | 15.98 | 0.28 |

TABLE 4

Virginiamycin control drop data - "Post Penicillin G test"

| Test # | Ferm # | Lactic % | Acetic % | EtOH v/v % | Glucose % |
|---|---|---|---|---|---|
| 1 | 3 | 0.48 | 0.03 | 15.42 | 0.26 |
| 2 | 4 | 0.43 | 0.05 | 15.78 | 0.33 |
| 3 | 5 | 0.67 | 0.03 | 15.59 | 0.25 |
| 4 | 1 | 0.50 | 0.04 | 15.56 | 0.33 |
| 5 | 2 | 0.40 | 0.05 | 15.52 | 0.26 |
| 6 | 3 | 0.44 | 0.04 | 15.57 | 0.35 |
| 7 | 4 | 0.64 | 0.04 | 15.53 | 0.29 |
| 8 | 5 | 0.53 | 0.03 | 15.45 | 0.35 |
| 9 | 1 | 0.70 | 0.03 | 15.28 | 0.32 |
| 10 | 2 | 0.68 | 0.04 | 15.24 | 0.30 |
| 10 | Batch average | 0.57 | 0.04 | 15.49 | 0.30 |

The fermentors (Set 2) treated with Penicillin G Procaine utilized the same amount of glucose, had a decrease in lactic acid and an increase in final ethanol production when compared to the fermentors (Sets 1 and 3) treated with the same amount of Virginiamycin. The data presented in tables 2 through 4 indicates that prior to the use of Penicillin G Procaine in fermentation, contaminating bacteria were utilizing a greater percentage of the available carbohydrate to produce lactic acid and less carbohydrate was available for the yeast fermentation. At 0.5 ppm as per table 1 Virginiamycin did not seem to inhibit the growth of the "industry normal" bacteria while the Penicillin G Procaine brought the desired results at around 0.1 ppm. This result in table 1 is substantiated by the actual controlled plant trials on the 3 sets of fermentors showing how Penicillin G Procaine affects fermentation and it's by products. During the Penicillin G Procaine trial, more carbohydrate was utilized by yeast for ethanol production. The "post trial" fermentors reflected a trend back towards lactic acid production by contaminating bacteria. Furthermore, during the Penicillin G Procaine trial, lactic acid production decreased by about a quarter percent while ethanol production increased by about half a percent representing a production increase of about 2,500 gallons of ethanol per fermentor.

Determination of Residuals of Bactenix V50, V60 or V60SP or V60SPK in Distillers Co-Products This experiment determined if any residual levels of the Penicillin G Procaine were found in distillers co-products derived from fermentation batches in Set 2 above, in which Penicillin G Procaine was used as an antimicrobial agent. These trials were conducted in a 50 m/g/y fuel ethanol producing facility utilizing corn as a substrate. This facility is a dry grind, batch fermentation process producing both dried distillers grains with solubles (DDGS) and wet distillers grains with solubles (WDGS) utilizing 0.5 ppm Penicillin G Procaine. Five samples consisted of four DDGS and one WDGS were taken from co-products produced by fermentation batches solely utilizing Penicillin G Procaine.

TABLE 5

Distillers co-product showing absence of antibiotic, Penicillin G Procaine

| Sample ID | Samples obtained from fermentation batches | Amount used in fermentation | Antimicrobial residual (limit 50 ppb) |
|---|---|---|---|
| DDGS #01 | 1 to 2 | 0.5 ppm | Not Detected |
| DDGS #02 | 2 to 3 | 0.5 ppm | Not Detected |
| DDGS #03 | 3 to 4 | 0.5 ppm | Not Detected |
| DDGS #04 | 4 to 5 | 0.5 ppm | Not Detected |
| WDGS #01 | 2 to 4 | 0.5 ppm | Not Detected |

All samples were refrigerated or maintained on ice packs preserving freshness and then shipped to Midwest Laboratories in Omaha, Nebr. USA. Midwest Labs utilized liquid chromatogram quadrupole mass spectrometry (LC/MS) to test the samples with a low detection limit of 50 parts per billion. No Penicillin was detected in any of the samples, indicating no Penicillin was carried through to distillers co-products. See results in Table 5 above.

Table 6 shows another trial from a fermentation ethanol production facility for residual level detection from the post fermentation derivatives which ultimately becomes the distillers grains, the residuals analyzed by Central Analytical Laboratories Metairie, La. The samples for testing were from predetermined positions at specific samples points in the ethanol process. The collected samples from the DDGS, WDGS, syrup and centrifuge solids were all samples from the corn residue after the removal of ethanol. The samples tested were from batches that used 0.785 ppm of Virginiamycin or 0.785 ppm of Penicillin G Procaine. The results of the two antibiotics in residues are shown in table 6 with a residual detection level of a 1.5 ppm minimum.

TABLE 6

Detection of residual level of Virginiamycin and Penicillin G Procaine antibiotics from the distillers grains at various sample points from Corn residue

| Trial Test # | Sample Point in Post Ferm Process | Virginiamycin introduced at 0.785 ppm | Penicillin G Procaine introduced at 0.785 ppm |
|---|---|---|---|
| 1 | DDGS | None detected | None detected |
| 2 | WDGS | 2.8 | None detected |
| 3 | Syrup | 3.3 | None detected |
| 4 | Centrifuge Solid | None detected** | None detected |

Note:
**Virginiamycin at 1.5 ppm minimum detection level showed the absence of any antibiotic in the centrifuge solid. However at another detection level of 0.2 ppm Virginiamycin was detected at 1.2 mg/kg compared to no detection for Penicillin G Procaine at this detection level.

Virginiamycin detection in the corn residue that is the distillers grains like DDGS, WDGS etc is of particular interest since the distillers grains can be added to the animal feed as animal feed ingredient. The corn residue at the end of fermentation may also contain other ingredients like unreacted enzymes, sugar, starch, certain organic acids, proteins matters, yeast, and a host of nutrients. It becomes a source of concern if the distillers grain is found to contain residues of antibiotics, albeit in minuscule amounts. The presence of antibiotics in the ingredients that form a part of an animal's daily ration can be perceived as detrimental to the animal's health and may be ultimately to human health. Because of such awareness efforts today are underway to find alternative sources of antimicrobials or antibiotics for use in fermentation processes. The non-detection of Penicillin G Procaine as an antibiotic which serves as a bacterial contaminant suppressant during the fermentation ethanol production and its subsequent degradation during the processing steps makes this method of use application a novel and unique finding that potentially can provide the end users with an option to further their manufacturing gains by being profitable on two accounts. The non-detection of Penicillin G Procaine even at a minimum detection level of 50 parts per billion (ppb) enables the distillers grain to augment the grain as a safe and useful ingredient that can now be part of a ration for a much diverse species of animals, birds and fish. This coupled with the immediate added benefit derived from an increase in the fuel ethanol yield through the fermentation process where the bacterial suppression liberates more glucose for its conversion to alcohol by the yeast present in the reaction mixture makes Penicillin G Procaine a suitable alternative to the detectable Virginiamycin at parts per million (ppm) levels in the post fermentation derivatives. Also, as can be deduced from the melting point decomposition of Penicillin G Potassium at >220 degrees C. and Penicillin G Procaine of a temperature of 106-110 degree C., in the event of any unreacted crystalline antibiotic found present in the wet residues, upon drying at elevated temperatures, Penicillin G Procaine will have a greater propensity to be inactive and subsequently decompose when compared to the Potassium salt of Penicillin.

Impact Comparison of Penicillin G Procaine and Penicillin G Potassium on the Function and Replication of *Saccharomyces cerevisiae* During Alcohol Production by Fermentation A study was conducted to determine the degree of impact of the fermentation antimicrobial Penicillin G Procaine and Penicillin G potassium during alcohol production by fermentation. The antimicrobial impact was inferred by conducting a series of fermentations and measuring if the above said antibiotics interfered with the cell growth and the fermentation function of *Saccharomyces cerevisiae* yeast used in the fermentation phase. This study provided analysis of what impact, if any, the Penicillin G Procaine or Penicillin G Potassium has on the yeast during lab scale fermentations, specifically BioFerm® XR yeast from North American Bioproducts Corporation (NABC). This study observed the ability of yeast to replicate and ferment a corn mash substrate with and without the presence of Penicillin G Procaine or Penicillin G Potassium.

Procedure:

This study was set up in a series of fermentation vessels. All antibiotic concentrations were tested in triplicate. Cell counts were done on one flask for each treatment at 12, 24, 36 and 48 hours and testing of the fermentation reactions by HPLC was also performed at 12, 24, 36 and 48 hours. The experiment was set as follows:

1. Antibiotic solutions were prepared to provide a sterile 1 and 10 µg/ml solutions.
2. Antibiotic solutions tested were as follows:
   A. Control (NAB-00), no antibiotic
   B. Penicillin G Potassium (PGK-05), 5 ppm
   C. Penicillin G Potassium (PGK-15), 15 ppm
   D. Penicillin G Potassium (PGK-30), 30 ppm
   E. Penicillin G Procaine (PGP-05), 5 ppm
   F. Penicillin G Procaine (PGP-15), 15 ppm
   G. Penicillin G Procaine (PGP-30), 30 ppm
3. Fermentations were set up using 31% solids corn mash using saccharifying enzymes and the following procedure:
   A. Yeast Conditioning:
     1. Add 2 g yeast to 10 ml sterile water for each 3 flasks to test, (14 g yeast to 70 ml water) into a sterile 250 ml flask and place in water bath set to 100° F.
     2. Incubate at 100° F. for 30 minutes with occasional mixing.
     3. Remove flasks from water bath and divide suspension between the all flasks for the trial.
   B. Fermentation Procedure
     1. To prepared mash, add the following.
       a. Add 0.58 g urea/liter mash and mix.
       b. Add 0.2 ml GA per liter and mix.
     2. Remove sample for background HPLC testing.
     3. Add antibiotic solution to labeled sterile 250 ml flasks.
     4. Add hydrated yeast suspension to mash and mix well.
     5. Add sterile stir bar to each flask and add about 150 ml mash into each 250 ml flask for a total of 21 flasks.
     6. Cover each flask with a gas trap in a sterilized stopper.
     7. Place in a 33° C. water bath with continuous mixing at 280 rpm at 75% power.
     8. Remove sample at 12 hr interval to perform cell count, viability and budding.
     9. Incubate sample up to 48 hours, enough time for complete fermentation
     10. Collect samples at the following times for cell counts and HPLC testing: 12 hours; 24 hours; 36 hours and 48 hours As displayed in Table 7, there was no discernable adverse effect of Penicillin G Procaine on the yeast when used up to 30 ppm, which is between six to 30 times the product's preferred dosage rates. The cell count data indicated that while there was some variation in cell counts, the viability and budding levels were comparable for the seven sample sets. The data also shows that the effect of antibiotics strengthens overall the cell count over time when compared to the trial where no antibiotic was used. Another noticeable difference at the highest concentration of 30 ppm of antibiotic use the cell counts tend to taper off when compared to the trials with lower concentration of antibiotics. Even though the antibiotic inclusion rates are seemingly high, this testing is relevant to the current invention because often times antibiotics are introduced to the fermentor during the fill cycle which will have a concentration effect that potentially equals these test rates. The possible ability of Penicillin G Procaine to release slowly in aqueous based systems under ambient conditions may be the differentiating performance in promoting and not causing deleterious effects on yeast fermentation.

TABLE 7

Impact comparison of Penicillin G Procaine and Penicillin G Potassium salt showing no hindrance in the growth of yeast cells

| Sample | CC^ | %V^ | %B^ | CC* | %V* | %B* | CC" | %V" | %B" | CC~ | %V~ | %B~ |
|---|---|---|---|---|---|---|---|---|---|---|---|---|
| NAB-00 | 604 | 87 | 16.5 | 559 | 85 | 7.3 | 471 | 80 | 6.6 | 466 | 74 | 6.1 |
| PGK-05 | 580 | 88 | 13.8 | 556 | 90 | 8.4 | 520 | 81 | 8.1 | 508 | 75 | 8.9 |
| PGK-15 | 552 | 85 | 13.3 | 541 | 86 | 7.5 | 530 | 82 | 6.2 | 516 | 72 | 7.3 |
| PGK-30 | 622 | 86 | 12.3 | 525 | 88 | 8.7 | 501 | 80 | 8.7 | 511 | 77 | 6.4 |
| PGP-05 | 601 | 89 | 15.0 | 556 | 88 | 7.9 | 521 | 83 | 9.2 | 538 | 75 | 8.0 |
| PGP-15 | 574 | 86 | 17.7 | 580 | 91 | 7.8 | 526 | 78 | 7.3 | 520 | 74 | 9.0 |
| PGP-30 | 621 | 85 | 14.8 | 557 | 89 | 10.3 | 513 | 78 | 7.0 | 493 | 78 | 6.0 |

Note:
1) Cell count (CC) is presented as the total number of cells in a given volume for 12 hr (^), 24 hr (*), 36 hr (") and 48 hr (~) fermentation samples.
2) % viability (%V) is presented as the percent of cells that are thriving in a given volume for 12 hr (^), 24 hr (*), 36 hr (") and 48 hr (~) fermentation samples.
3) % budding (%B) is presented as the percent of daughter cells developed from the mother cells for 12 hr (^), 24 hr (*), 36 hr (") and 48 hr (~) fermentation sample.

The expected population dynamics in the samples between 12, 24, 36 and 48 hours for viability and budding percent for all sample sets are very similar. The cell count after the 24 hour mark for a few antibiotic trials does not seem to fit the trend as seen for the PGK-30 and PGP-05 trials. Although the cell count variations for these two trials are nominal this may be due to the antibiotic effect or its relation to viability percent or a combination of sampling and recording artifact and not an actual variation for these samples. Based on the data from table 7 however it can be deduced that with increasing fermentation time the yeast growth is better when the environment has Penicillin G antibiotic present. The viability and budding rates show a gradual decline by and large as expected for batch process fermentations.

The fermentation samples at intervals of 12 hours up to 48 hours as shown in table 7 presented the cell counts, viability and budding of the yeast during the fermentation process. Table 8 shows an averaged yeast cell count, yeast % viability and yeast % budding for the four sample points in the laboratory trial.

logically active growth and multiplication, an overwhelming support for the use of antibiotic at low concentrations to control the bacteria to facilitate the yeast metabolism and performance.

A closer comparison between the Penicillin G Procaine and Penicillin G Potassium averages implies superior compatibility of the Procaine type of Penicillin in terms of the cell counts, viability and budding of the yeast.

It may be perceived that by controlling the bacteria around the yeast and minimizing the bacterial competition for the sugar used for yeast functioning and metabolism, the antibiotic and in particular Penicillin G Procaine is able to facilitate yeast growth and multiplication at an elevated level when compared to Penicillin G Potassium in three fundamental areas: cell presence, ability to live, and ability to reproduce. This phenomenon is of critical importance to the production of alcohol by fermentation as very often yeast must competitively exclude contaminating bacteria in all stages of fermentation in order to obtain consistent, efficient, and high yielding alcohol fermentations.

TABLE 8

Comparative effect of Penicillin G Procaine and Penicillin G Potassium on the yeast cell count, viability and budding (reproducing ability) in a laboratory fermentation trial

| Sample | ACC | A%V | A%B |
|---|---|---|---|
| NAB-00 | 525 | 81.5 | 9.1 |
| PGK-05 | 541 | 83.5 | 9.8 |
| PGK-15 | 535 | 81.3 | 8.6 |
| PGK-30 | 540 | 82.8 | 9.0 |
| APGK | 539 | 82.5 | 9.1 |
| PGP-05 | 554 | 83.8 | 10.0 |
| PGP-15 | 550 | 82.3 | 10.4 |
| PGP-30 | 546 | 82.5 | 9.5 |
| APGP | 550 | 82.8 | 10.0 |

Note:
1) Average cell count (ACC) is presented as the average of the total number of cells in a given volume for 12, 24, 36 and 48 hour fermentation samples.
2) Average % viability (A%V) is presented as the average of the percent of cells that are thriving in a given volume for 12, 24, 36 and 48 hour fermentation samples.
3) Average % budding (A%B) is presented as the average of the percent of daughter cells developed from the mother cells for 12, 24, 36 and 48 hour fermentation samples.
4) APGK and APGP are the averages for all the three trials of the antibiotics at the different concentrations.

TABLE 9

Comparative effect of Penicillin G Procaine and Penicillin G Potassium on the viable yeast cell count at 12 hour time intervals in a laboratory fermentation trial

| Sample | 12 hours | 24 hours | 36 hours | 48 hours | Average 12-48 hours |
|---|---|---|---|---|---|
| NAB-00 | 525 | 475 | 377 | 345 | 431 |
| PGK-05 | 510 | 500 | 421 | 381 | 453 |
| PGK-15 | 469 | 465 | 435 | 372 | 435 |
| PGK-30 | 535 | 462 | 401 | 393 | 448 |
| APGK | 505 | 476 | 419 | 382 | 445 |
| PGP-05 | 535 | 489 | 432 | 404 | 465 |
| PGP-15 | 494 | 528 | 410 | 385 | 454 |
| PGP-30 | 528 | 496 | 400 | 385 | 452 |
| APGP | 519 | 504 | 414 | 391 | 457 |

Note:
1) Live or viable yeast cell count is calculated by multiplying the total observed cell count by the % viability.
2) The viable cell count in each column is for the 12, 24, 36 and 48 hour fermentation samples. Last column shows the average of the four samples between 12-48 hours of the fermentation trial.
3) APGK and APGP are the averages for all the three trials of the antibiotics at the different concentrations.

As expected, however, both the Procaine and the potassium salts work favorably for the propagation of the yeast during the fermentation trials. Results of the averages in table 8 showing the three components of yeast measured and tabulated are favorable for trials with Penicillin G Procaine. The results indicate, accounting for fermentation variation, bio- The proper functioning of the yeast is often attributed to the higher efficiency with which it can convert the sugars formed in a fermentation process to the desired alcohol. Also the number of yeast cells in a fermentation mix is an important factor as it will be entropically favored to convert the available sugar molecules to ethanol and carbon dioxide. The sugar in the fermentation mix apart from being converted to ethanol is also used by the yeast for its metabolism and growth and by the concerned "industry normal" *Lactobacillus fermentum* bacteria converting the sugar to lactic acid. Table 10 shows the laboratory fermentation data comparing the two Penicillin G types of antibiotics as well as a trial without antibiotic, measuring the desired ethanol and the undesired lactic acid produced.

TABLE 10

Comparative effect of Penicillin G Procaine and Penicillin G Potassium on the formation of alcohol and lactic acid in a laboratory fermentation trial

| Sample | Time in hours | % Lactic Acid | % wt EtOH |
|---|---|---|---|
| NAB-00 | 12 | 0.081 | 5.98 |
|  | 24 | 0.101 | 9.04 |
|  | 36 | 0.111 | 11.02 |
|  | 48 | 0.107 | 11.70 |
| PGK-05 | 12 | 0.083 | 6.16 |
|  | 24 | 0.100 | 9.12 |
|  | 36 | 0.108 | 11.12 |
|  | 48 | 0.104 | 11.89 |
| PGK-15 | 12 | 0.081 | 6.05 |
|  | 24 | 0.100 | 9.15 |
|  | 36 | 0.105 | 11.05 |
|  | 48 | 0.100 | 11.92 |
| PGK-30 | 12 | 0.082 | 6.07 |
|  | 24 | 0.096 | 9.13 |
|  | 36 | 0.106 | 11.12 |
|  | 48 | 0.101 | 11.83 |
| PGP-05 | 12 | 0.082 | 6.21 |
|  | 24 | 0.098 | 9.24 |
|  | 36 | 0.108 | 11.14 |
|  | 48 | 0.104 | 11.94 |
| PGP-15 | 12 | 0.085 | 6.16 |
|  | 24 | 0.099 | 9.13 |
|  | 36 | 0.106 | 11.13 |
|  | 48 | 0.099 | 11.98 |
| PGP-30 | 12 | 0.081 | 6.34 |
|  | 24 | 0.098 | 9.16 |
|  | 36 | 0.103 | 11.18 |
|  | 48 | 0.100 | 11.91 |

Note:
1) Fermentation results at 12 hour intervals for the different concentrations of antibiotics used showing the levels of lactic acid and ethanol formed during the fermentation process.
2) The samples were taken and measured ethanol and lactic acid at the 12th, 24th, 36$^{th}$ and 48th hour of the fermentation.

In the absence of any antibiotic in the fermentation mix the generation of higher amount of lactic acid is noticed with a corresponding lower amount of ethanol produced at the four sample points compared to the rest of the trials. Towards the end of fermentation time, at the 48 hour mark the Penicillin G Procaine added trials at 3 different concentrations outperform its corresponding Penicillin G Potassium trials for the quantities of ethanol produced.

Although the difference in alcohol produced seems inconsequential in lab scale fermentation, it nonetheless becomes a more preferred antibiotic as its effect on an industrial scale fermentation process is greatly multiplied due to process scale up, higher process efficiency and product yield consistency. This consistent higher ethanol yield as observed in most of the fermentation time intervals for the added Penicillin G Procaine trials when compared to its corresponding potassium salt trials also show a lower residue of lactic acid formed. The lower lactic acid formations indicate the efficient bacterial contaminant suppressing ability of the Penicillin G Procaine over longer period of time complimented by higher ethanol yield in these trials.

The higher yields of alcohol produced may be accredited to the robust yeast metabolism, efficient use of available sugar by the yeast, lower multiplication of bacteria and presence of higher amounts of sugar due to less significant consumption by bacteria all of which are either directly or indirectly affected by the Penicillin G Procaine functioning to enhance and drive the fermentation mixture to the desired product.

This control of unwanted *Lactobacillus fermentum* bacteria and the higher viable yeast cells in the presence of Penicillin G Potassium antibiotic environment contributes towards the production of higher amounts of alcohol as can also be inferred from the plant trial data in table 3.

Strength Comparison of Penicillin G Procaine and Penicillin G Potassium in Bacterial Inhibition Test To directly measure the efficacy of Penicillin G Procaine and Penicillin G Potassium a bacterial inhibition test was designed using industrial isolates and chosen ATCC strains. The inhibition testing was spread over 0.1 ppm to 5.0 ppm for the *Lactobacillus fermentum* and 1.0 ppm to 5.0 ppm for *Lactobacillus brevis* species of bacteria due to the lack of response of *Lactobacillus brevis* at lower concentrations. As examples for demonstration, specifically for this inhibition testing, industry familiar bacteria were chosen among the various known and isolated bacteria from the ethanol plants. The strains used were two isolates of *Lactobacillus fermentum* and 2 isolates of *Lactobacillus brevis*. The *Lactobacillus fermentum* series contained both an industry derived isolate Ind 1 and an ATCC strain while the *Lactobacillus brevis* series comprised of two isolates, Ind 1 and Ind 43 derived from the ethanol plants. The inhibition test plates were set in triplicate and read at 12 hour intervals up to 48 hours of test endpoint. The results below represent the mode average of the outcome from the triplicate inhibitory test sets for each trial. Table 11 lists the *Lactobacillus fermentum* and the *Lactobacillus brevis* results of the inhibition testing as follows: successful test corresponding to no growth is represented as (−), barely discernable growth is represented as (±) and easily noticeable bacterial growth is represented as (+). The set of control tests depict (−) control as just broth and (+) control as just broth with bacteria but without any antibiotic.

The trial was set up as follows:
1. Weigh out 0.1 g of each sample to be tested into a 15 ml centrifuge tube.
2. Dissolve sample into 10 ml sterile water. If sample does not dissolve, use 10 ml of 50:50 ethanol-water.
   a. Add antibiotic to clean tube, add 2 ml water.
   b. Vortex, if antibiotic goes into solution add water for final volume of 10 ml.
   c. If material does not readily go into solution, add 5 ml 100 absolute ethanol and water for final volume of 10 ml.
   d. Vortex until all material is in solution.
3. Vortex the solutions to make sure that they are well mixed.
4. Filter the solutions through a 0.2 μm syringe filter into a second labeled sterile centrifuge tube.
5. Add antibiotic solution to MRS Broth for a final volume of 10 ml at the test concentration for each antibiotic.
6. Mix organism solutions and add 2 μl to each of 3 wells of a 24 well plate. If tubes are used add the 2 μl to each of three tubes for each antibiotic.
7. Transfer 1 ml of the antibiotic-broth solution to each well containing bacteria.
8. Recap remaining antibiotic solution and return the tube to the tube rack. This tube will become the negative control for each dilution created.
9. Add four μl of each bacterial culture to another set of wells and add four ml of broth without antibiotics. These wells will be the positive controls.

10. Incubate plates and tubes at 33 C for 48 hours, examining all samples at 24 hours for growth. Any turbidity detected should be a result of bacterial growth.

in this trial with the *Lactobacillus fermentum* isolate at lower levels of antibiotics substantiating Procaine Penicillin affects the bacteria for longer time period as shown in table 11.

TABLE 11

Bacterial Inhibition test on *L. fermentum* and *L. brevis* showing efficacy of Penicillin G Procaine over Penicillin G Potassium

| PGK | 0.1 ppm | | | | 0.3 ppm | | | | 0.5 ppm | | | | 1.0 ppm | | | | 5.0 ppm | | | |
|---|---|---|---|---|---|---|---|---|---|---|---|---|---|---|---|---|---|---|---|---|
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| Ind 1 *L. fermentum* | = | ± | ± | ± | = | = | ± | ± | = | = | = | = | = | = | = | = | = | = | = | = |
| PGP | 0.1 ppm | | | | 0.3 ppm | | | | 0.5 ppm | | | | 1 ppm | | | | 5 ppm | | | |
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| Ind. 1 *L. fermentum* | = | ± | ± | ± | = | = | = | ± | = | = | = | = | = | = | = | = | = | = | = | = |
| PGK | 0.1 ppm | | | | 0.3 ppm | | | | 0.5 ppm | | | | 1 ppm | | | | 5 ppm | | | |
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| ATCC *L. fermentum* | = | = | ± | ± | = | = | = | = | = | = | = | = | = | = | = | = | = | = | = | = |
| PGP | 0.1 ppm | | | | 0.3 ppm | | | | 0.5 ppm | | | | 1 ppm | | | | 5 ppm | | | |
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| ATCC *L. fermentum* | = | = | = | ± | = | = | = | = | = | = | = | = | = | = | = | = | = | = | = | = |
| PGK | 1 ppm | | | | 2 ppm | | | | 3 ppm | | | | 4 ppm | | | | 5 ppm | | | |
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| Ind 1 *L. brevis* | ± | + | + | + | ± | + | + | + | ± | + | + | + | ± | + | + | + | = | = | ± | + |
| PGP | 1 ppm | | | | 2 ppm | | | | 3 ppm | | | | 4 ppm | | | | 5 ppm | | | |
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| Ind 1 *L. brevis* | ± | + | + | + | ± | + | + | + | ± | + | + | + | ± | ± | + | + | = | = | ± | + |
| PGK | 1 ppm | | | | 2 ppm | | | | 3 ppm | | | | 4 ppm | | | | 5 ppm | | | |
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| Ind 43 *L. brevis* | = | + | + | + | = | + | + | + | = | + | + | + | = | ± | ± | + | = | ± | ± | + |
| PGP | 1 ppm | | | | 2 ppm | | | | 3 ppm | | | | 4 ppm | | | | 5 ppm | | | |
| Inc Time | 12 | 24 | 36 | 48 | 12 | 24 | 36 | 48 | 12 | 24 | 36 | 48 | 12 | 24 | 36 | 48 | 12 | 24 | 36 | 48 |
| Ind 43 *L. brevis* | = | + | + | + | = | + | + | + | = | + | + | + | = | ± | + | + | = | ± | ± | + |
| + control | + | + | + | + | + | + | + | + | + | + | + | + | + | + | + | + | + | + | + | + |
| − control | = | = | = | = | = | = | = | = | = | = | = | = | = | = | = | = | = | = | = | = |

As shown in table 11, the performance of Penicillin G Procaine in suppressing the bacterial growth of *Lactobacillus fermentum*, both for ATCC and industry isolates (Ind #) in and of the two *Lactobacillus brevis* industrial isolates was found to be superior to the Penicillin G Potassium in the test media. As can be noted from table 11, there is a trend observed for longer sustainability of the antibiotic Penicillin G Procaine in the test media when compared to the Penicillin G Potassium depicted by the slightly longer effective control of bacteria by Penicillin G Procaine in most isolates under the different antibiotic concentration. None of the antibiotics showed any acceptable bacterial suppressing ability below 3 ppm when tested on the *Lactobacillus brevis* species over the 48 hours. But at higher dosage the effectiveness of the antibiotics towards *Lactobacillus brevis* become more prominent enabling an easier comparison between the two antibiotics. The sustained effectiveness of Procaine Penicillin is indicated All of the compositions and/or methods disclosed and claimed herein can be made and executed without undue experimentation in light of the present disclosure. While the compositions and methods of this invention have been described in terms of specific embodiments, it will be apparent to those of skill in the art that variations of the compositions and/or methods and in the steps or in the sequence of steps of the method described herein can be made without departing from the concept, spirit and scope of the invention. All such similar substitutes and modifications apparent to those skilled in the art are deemed to be within the spirit, scope and concept of the invention as defined by the appended claims.

The invention claimed is:

1. A method for controlling the growth of *Lactobacillus* species in a fermentation process for the production of ethanol comprising the steps of:

adding a minimum inhibitory concentration of Penicillin G Procaine to a vessel wherein Penicillin G Procaine becomes part of a fermentation mixture, and wherein the fermentation mixture includes *Saccharomyces cerevisiae* yeast for making ethanol;

maintaining the fermentation mixture at a temperature between 30-38° C. and at a pH of between 2.5 to 8 during the fermentation process for producing ethanol, wherein the concentration of Penicillin G Procaine ranges from 0.1 ppm to about 5 ppm of the fermentation mixture, wherein the vessel is susceptible to contamination by *Lactobacillus* species, and wherein the addition of the minimum inhibitory concentration of Penicillin G Procaine to the vessel controls the growth of *Lactobacillus* species while not having deleterious effects on the *Saccharomyces cerevisiae* yeast in the fermentation mixture during the fermentation process for producing ethanol; and recovering the ethanol and distillers co-products with no detectable level of Penicillin G Procaine from the fermentation mixture.

\* \* \* \* \*